United States Patent [19]
Gregorio et al.

[11] 3,968,134
[45] July 6, 1976

[54] PROCESS FOR RECOVERING CATALYST SYSTEMS FROM RAW HYDROFORMYLATION PRODUCTS

[75] Inventors: Guglielmo Gregorio, Milan; Giorgio Montrasi, Gabagnate Milanese (Milan), both of Italy

[73] Assignee: Montedison S.p.A., Milan, Italy

[22] Filed: Jan. 22, 1975

[21] Appl. No.: 543,151

[30] Foreign Application Priority Data
Jan. 23, 1974    Italy .................................. 19691/74

[52] U.S. Cl. ...................... 260/429 R; 260/606.5 P
[51] Int. Cl.$^2$ ........................................ C07F 15/00
[58] Field of Search .................. 260/429 R, 606.5 P

[56] References Cited
UNITED STATES PATENTS

| | | | |
|---|---|---|---|
| 3,515,757 | 6/1970 | Sibert | 260/429 R X |
| 3,547,964 | 12/1970 | Olivier | 260/429 R |
| 3,560,539 | 2/1971 | Booth | 260/429 R |
| 3,755,393 | 8/1973 | Kniese et al. | 260/429 R |

Primary Examiner—Helen M. S. Sneed

[57] ABSTRACT

Complexes of transition metals with organic ligands are recovered from raw reaction products containing the complexes, and in particular such complexes of rhodium with tertiary phosphines are recovered from raw hydroformylation products. The raw hydroformylation product (or if such product is subjected to distillation, the tails of the distillation) are treated with an aqueous solution of an aldehyde having from 1 to 4 carbon atoms and of a strong acid and the solid rhodium complex thus formed is separated by filtration.

6 Claims, No Drawings

PROCESS FOR RECOVERING CATALYST SYSTEMS FROM RAW HYDROFORMYLATION PRODUCTS

THE PRIOR ART

Soluble complexes of transition metals, in particular of rhodium, with simple or substituted tertiary phosphines as ligands, are useful catalysts in the hydroformylation of olefins. Usually, such complexes are employed in the presence of ligand in excess of the amount bound in the complex and, consequently, it is necessary to recover the catalyst system due to the high cost of both the metal and organic ligand.

It is known that tertiary phosphines, being weak bases, can be extracted from organic liquids containing them by means of aqueous solutions of mineral acids.

That method has the disadvantage that recovery of triphenylphosphine from raw reaction products containing it as ligand of rhodium complexes requires the use of aqueous solutions of relatively high concentration and a large excess of the mineral acids.

It is also known that tertiary phosphines form, by reaction with aqueous acid solutions of aldehydes, particularly formaldehyde, adducts of the phosphonium salt type, according to the following reaction scheme:

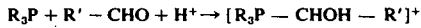

The phosphine can be recovered from those adducts by the simple addition of basic compounds.

THE PRESENT INVENTION

An object of this invention is to provide a simple, economical process for recovering complexes of rhodium and triphenylphosphine in readily reusable form from raw hydroformylation products or from the distillation tails when the raw products are subjected to distillation for separating the desired products from the raw hydroformylation products.

This and other objects are accomplished by the present invention in accordance with which the organic liquid containing the raw hydroformylation products, or the distillation tails, is treated with an aqueous solution of an aldehyde having from 1 to 4 carbon atoms and of a strong acid, in a molar ratio of from 1:1 to 1:3 with respect to the phosphine, at a temperature of from 60°C to 150°C, and then separating the solid rhodium complex thus formed by filtration and the triphenylphosphine-containing aqueous solution by decantation. Solid triphenylphosphine containing traces of rhodium compounds can be obtained by alkalinization of the aqueous solution.

Both the triphenylphosphine so extracted and the solid rhodium complex can be re-employed as catalyst system in further hydroformylation reactions.

Aldehydes useful in the practice of this invention are preferably aliphatic aldehydes containing from 1 to 4 carbon atoms, in particular formaldehyde, isobutyraldehyde, etc.

The acids useful in the process are strong mineral acids, in particular hydrochloric, sulphuric and perchloric acids.

The temperature at which the treatment with the aqueous solution of the aldehyde, and of the mineral acid, is carried out can vary between 60°C and 150°C, preferably between 80°C and 100°C. It is particularly advantageous to operate at the boiling point of the mixture containing the rhodium/triphenylphosphine complex and excess triphenylphosphine.

The reaction may be carried out in air but is preferably carried out in an inert gas atmosphere, such as nitrogen or carbon monoxide.

According to a presently preferred embodiment of this invention, a mixture of high-boiling compounds coming from the hydroformylation of olefins from which the desired products have been distilled off and containing triphenylphosphine and rhodium in the form of soluble complexes (hydrides and carbonyls bound to triphenylphosphine) is treated under boiling with an aqueous solution containing formaldehyde and hydrochloric acid in a molar ratio of 1:1 with respect to phosphine.

At the end of the reaction, a solid crystalline and sparingly soluble complex of rhodium-carbonylphosphine—chloride, having the formula $Rh(CO)Cl(PPh_3)_2$ is separated by filtration at room temperature, while the aqueous solution is separated by decantation and alkalized in order to extract solid triphenylphosphine containing traces of rhodium compounds which have passed into the aqueous solution.

The $Rh(CO)Cl(PPh_3)_2$ compound can be either easily transformed again into one of the zero-valent hydride or carbonyl complexes suitable to be utilized as hydroformylation catalysts, or directly employed in the hydroformylation reaction in case it is operated in the presence of an organic base to bind the chlorine atom.

The amount of recovered product depends on the solubility and on the initial concentration of rhodium.

If the acid employed is sulphuric acid, sparingly soluble solid complexes of rhodium carbonylphosphine form; such complexes exhibit, unlike the complex obtained by treatment with HCl, a low solubility in water. In that case, a portion of rhodium passes into the aqueous solution (in an amount depending upon the amount of the acid used), and it is possible to recover it from the aqueous solution together with the triphenylphosphine by a simple alkaline treatment, in directly re-usable form.

The following examples are given to illustrate the invention, and are not intended to be limiting.

EXAMPLE 1

100 cc of a mixture of aldehydes and other high-boiling compounds coming from propylene hydroformylation and from which n- and iso-butyraldehydes were recovered by distillation, contained 400 mg of rhodium in the form of soluble complexes (hydrides and carbonyls bound to triphenylphosphine) and 18 g of triphenylphosphine.

Such mixture was treated with 100 cc of an aqueous solution of 1 mol. formaldehyde and 1 mol. hydrochloric acid. After boiling for 15 minutes it was filtered. 2.6 g of solid $Rh(CO)Cl(PPh_3)_2$ (96% of the theoretical) were thus obtained. The aqueous solution was decanted from the filtrate and was treated with sodium carbonate until alkaline reaction.

16.5 g of solid triphenylphosphine containing traces of rhodium compounds were separated, filtered, washed with water and dried under vacuum for use in a successive hydroformulation reaction.

The rhodium carbonylphosphine — chloride complex was directly re-used in a hydroformylation reaction in the presence of a stoichiometric amount of an organic base to bind the chlorine atom.

EXAMPLE 2

Example 1 was repeated, but using sulphuric acid instead of hydrochloric acid. A crystalline complex of rhodium and triphenylphosphine containing 93% of the initial rhodium precipitated. A portion of rhodium passed into aqueous solution and was precipitated along with the phhosphine in a form soluble in the organic solvents and re-employable in another hydroformylation reaction.

What we claim is:

1. A process for recovering complexes of rhodium and triphenylphosphine from the organic liquid comprised in raw hydroformylation products of olefins, or in tails resulting from distillation of said raw products, which comprises treating the organic liquid containing the complexes of rhodium and triphenylphosphine with an aqueous solution of an aldehyde having from 1 to 4 carbon atoms and of a strong mineral acid, in a molar ratio of from 1:1 to 1:3 with respect to the phosphine, at a temperature of from 60°C to 150°C, separating by filtration the solid rhodium complex which forms during the treatment with the aqueous aldehyde and acid solution, and separating the aqueous solution containing triphenylphosphine by decantation.

2. The process of claim 1 in which the aldehyde is an aliphatic aldehyde.

3. The process of claim 1, in which the aldehyde is formaldehyde or isobutyraldehyde.

4. The process of claim 1, in which the strong acid is hydrochloric acid, sulphuric acid or perchloric acid.

5. The process of claim 1, in which the aldehyde and the acid are used in a molar ratio of 1:1 with respect to the phosphine.

6. The process of claim 1, in which the treating temperature is from 80°C to 100°C.

* * * * *